(12) United States Patent
Li et al.

(10) Patent No.: US 12,276,661 B2
(45) Date of Patent: Apr. 15, 2025

(54) TIME-RESOLVED FLUORESCENCE IMMUNOCHROMATOGRAPHY KIT FOR SIMULTANEOUS DETECTION OF MIXED POLLUTANT OF AFLATOXIN AND CARBARYL, PREPARATION METHOD THEREFOR, AND APPLICATION THEREOF

(71) Applicant: OILCROPS RESEARCH INSTITUTE OF CHINESE ACADAMY OF AGRICULTURE SCIENCES, Hubei (CN)

(72) Inventors: Peiwu Li, Hubei (CN); Xiaoqian Tang, Hubei (CN); Qi Zhang, Hubei (CN); Zhaowei Zhang, Hubei (CN)

(73) Assignee: OILCROPS RESEARCH INSTITUTE OF CHINESE ACADAMY OF AGRICULTURE SCIENCES, Hubei (CN)

( * ) Notice: Subject to any disclaimer, the term of this patent is extended or adjusted under 35 U.S.C. 154(b) by 1399 days.

(21) Appl. No.: 16/634,315

(22) PCT Filed: Dec. 28, 2017

(86) PCT No.: PCT/CN2017/119440
§ 371 (c)(1),
(2) Date: Jan. 27, 2020

(87) PCT Pub. No.: WO2018/121677
PCT Pub. Date: Jul. 5, 2018

(65) Prior Publication Data
US 2021/0132058 A1    May 6, 2021

(30) Foreign Application Priority Data
Dec. 31, 2016 (CN) .......................... 201611268788.X

(51) Int. Cl.
*G01N 33/543* (2006.01)
*G01N 21/64* (2006.01)
(Continued)

(52) U.S. Cl.
CPC ....... *G01N 33/54388* (2021.08); *G01N 21/64* (2013.01); *G01N 33/543* (2013.01); *G01N 33/577* (2013.01); *C07K 16/44* (2013.01)

(58) Field of Classification Search
CPC .............. G01N 33/54388; G01N 21/64; G01N 33/543; G01N 33/577; G01N 2021/7786;
(Continued)

(56) References Cited

FOREIGN PATENT DOCUMENTS

| CN | 1523356 A | 8/2004 |
|---|---|---|
| CN | 1687782 A | 10/2005 |

(Continued)

OTHER PUBLICATIONS

Goel et al. ("Plasticity within the Antigen Combining Site May Manifest as Molecular Mimicry in the Humoral Immune Response," The Journal of Immunology (2004), 173(12):7358-7367) (Year: 2004).*

(Continued)

*Primary Examiner* — Christopher L Chin
(74) *Attorney, Agent, or Firm* — Troutman Pepper Locke LLP; Tim Tingkang Xia, Esq.

(57) ABSTRACT

A time-resolved fluorescence immunochromatography kit for the simultaneous detection of a mixed pollutant of aflatoxin and carbaryl, a preparation method therefor, and an application thereof. The kit comprises a time-resolved fluorescence immunochromatography test strip and a sample reaction vial containing a europium-labeled anti-aflatoxin monoclonal antibody and a europium-labeled anti-carbaryl monoclonal antibody lyophilized product, detection lines of the time-resolved fluorescence immunochromatography test (Continued)

strip being coated with an aflatoxin-bovine serum albumin conjugate and a carbaryl-ovalbumin conjugate respectively, and the anti-carbaryl monoclonal antibody is produced by secretion of a hybridoma cell line Jnw1D2 with a preservation number of CCTCC NO. C201654. The kit can be used for the simultaneous detection of aflatoxin and carbaryl content in a sample, and features simple and quick operations and a high sensitivity.

10 Claims, 1 Drawing Sheet
Specification includes a Sequence Listing.

(51) Int. Cl.
*G01N 33/577* (2006.01)
*C07K 16/44* (2006.01)

(58) Field of Classification Search
CPC .......... G01N 21/6408; G01N 21/8483; G01N 2333/38; G01N 2430/10; G01N 2430/60; G01N 33/56961; G01N 33/558; G01N 33/54387; G01N 33/54389; C07K 16/44; C07K 16/14; B01L 2300/0825
USPC ....... 422/400, 401, 420, 421, 425, 426, 430; 435/6.15, 287.7, 287.9, 970, 805, 810; 436/169, 170, 514, 518, 530, 810, 815
See application file for complete search history.

(56) References Cited

FOREIGN PATENT DOCUMENTS

| | | |
|---|---|---|
| CN | 101993855 A | 3/2011 |
| CN | 103257230 A | 8/2013 |
| CN | 103278630 A | 9/2013 |
| CN | 103278631 A | 9/2013 |
| CN | 105486858 A | 4/2016 |
| CN | 105652005 A | 6/2016 |
| CN | 106918704 A | 7/2017 |

OTHER PUBLICATIONS

Lloyd et al. ("Modelling the human immune response: performance of a 1011 human antibody repertoire against a broad panel of therapeutically relevant antigens," Protein Engineering, Design & Selection (2009), 22(3):159-168 (Year: 2009).*
Edwards et al. ("The remarkable flexibility of the human antibody repertoire; isolation of over one thousand different antibodies to a single protein, BlyS," Journal of Molecular Biology (2003), 334:103-118) (Year: 2003).*
Qu, Qiaoyu, "Study on the Immunoassay Technology for N-methylcarbamate Insecticide Carbaryl and Carbofuran Pesticide Residue", Jun. 2014, Chinese Academy of Agricultural Sciences Dissertation, China.
State Intellectual Property Office of People's Republic of China, "International Search Report for PCT Application No. PCT/CN2017/119440", China, Mar. 13, 2018.

\* cited by examiner

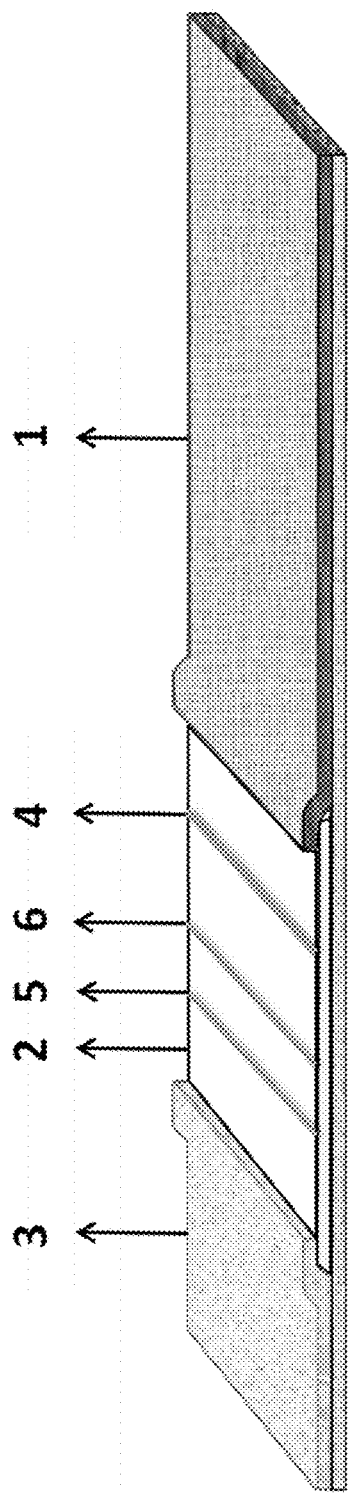

TIME-RESOLVED FLUORESCENCE IMMUNOCHROMATOGRAPHY KIT FOR SIMULTANEOUS DETECTION OF MIXED POLLUTANT OF AFLATOXIN AND CARBARYL, PREPARATION METHOD THEREFOR, AND APPLICATION THEREOF

SEQUENCE LISTING

This application includes a Sequence Listing in the ASCII text file in .txt format that is electronically submitted via EFS-Web on Aug. 9, 2024. The ASCII text file contains a sequence listing entitled "0123389183US9UpdatedSequenceListing.txt" created on Aug. 9, 2024 and is 3,895 bytes in size. The Sequence Listing contained in this 0123389183US9UpdatedSequenceListing.txt file is part of the specification and is hereby incorporated by reference herein in its entirety.

TECHNICAL FIELD

The application specifically relates to a time-resolved fluorescence immunochromatography kit for simultaneously detecting mixed pollution of aflatoxin and carbaryl, and a preparation method and application thereof.

BACKGROUND

Aflatoxin is a kind of main mycotoxin pollutants with high toxicity and wide pollution, and is divided as a kind of carcinogen by World Health Organization. The toxicity of aflatoxin is manifested in carcinogenesis, mutagenesis and teratogenesis in animals, and cause of DNA damage and immunosuppression. Aflatoxin pollution may occur at various stages of plantation, harvest and storage, transportation, consumption, etc., the polluted products mainly are cereals and nuts, and aflatoxin is also detected in other products such as meat, egg, and milk. Carbaryl is a kind of carbamates pesticide widely used in crops such as vegetables, fruits, cereals, etc., and has a good control effect on pests; however because of its abuse and prohibited use in agricultural production, carbaryl poses a significant threat to people's food safety, thus China established the maximum concentration of 0.5-1 μg/mL for carbaryl in cereals, and 1 μg/mL in vegetable. Aflatoxin and carbaryl in cereals tend to result in simultaneous pollution, there is a need to develop a convenient and efficient test technology for simultaneously detecting the two kinds of pollutants.

At present, the test methods for aflatoxin and carbaryl mainly consist of liquid chromatography, gas chromatography-mass spectrometry method, liquid chromatography-mass spectrometry method, etc. These methods have good stability, high sensitivity, and good accuracy, but pretreatment step is complicated, and sample test cost is high. Immunochromatographic method overcomes the above-described shortcomings, and is based on antigen-antibody specific reaction, wherein antigen is fixed by cellulose nitrate, and in chromatography process, free target substance and antigen on a test line competitively bind with labeled antibody, and content of the target substance in the sample is calculated on the basis of the amount of labeled substance binding onto the test line.

SUMMARY

The problem to be solved by the application is to provide a time-resolved fluorescence immunochromatography kit which may simultaneously detect mixed pollution of aflatoxin and carbaryl, and a preparation method and application thereof. The time-resolved fluorescence immunochromatography kit may be used in synchronous detection of contents of aflatoxin and carbaryl in a sample, and has the characteristics of simple and fast operation, and high sensitivity.

In order to solve the above-described technical problems, a technical scheme adopted by the present application is as below:

A time-resolved fluorescence immunochromatography kit for simultaneously detecting mixed pollution of aflatoxin and carbaryl, wherein the immunochromatographic time-resolved fluorescence immunochromatography kit comprises an immunochromatographic time-resolved fluorescent test strip, and a sample reaction vial containing a europium-labeled anti-aflatoxin monoclonal antibody freeze-dried product and a europium-labeled anti-carbaryl monoclonal antibody freeze-dried product, wherein the immunochromatographic time-resolved fluorescent test strip comprises a paperboard, an absorbent pad, a test pad and a sample pad are successively stuck onto one side of the paperboard from top to bottom, adjacent pads are overlapped and connected at junctions, the test pad uses a nitrocellulose membrane as a base pad, quality control line and test lines are arranged transversely on the nitrocellulose membrane from top to bottom, the quality control line is coated with a rabbit anti-mouse polyclonal antibody, the test lines are located below the quality control line, the number of the test lines is 2, and the test lines are respectively coated with an aflatoxin-bovine serum albumin conjugate and a carbaryl-ovalbumin conjugate; the anti-carbaryl monoclonal antibody is secreted by a hybridoma cell strain Jnw1D2 with an accession number of CCTCC NO. C201654. The hybridoma cell strain was stored/deposited under the terms of the Budapest Treaty on Mar. 29, 2016 at China Center for Type Culture Collection (CCTCC) in Wuhan University, Wuhan, China, one of recognized International Depository Authorities (IDAs), and has an accession number of CCTCC NO: C201654. The hybridoma cell strain Jnw1D2 will be irrevocably and without restriction or condition released to the public upon the issuance of a patent would satisfy the deposit requirement made herein.

According to the above-described technical scheme, the europium-labeled anti-carbaryl monoclonal antibody is prepared according to the following method: subjecting an anti-carbaryl monoclonal antibody and an activated europium-labeling reagent to an oscillatory reaction in a boric acid buffer solution for 2 hours or more, performing centrifuging to remove supernatant, and performing sealing to obtain a target product; and the europium-labeled anti-aflatoxin monoclonal antibody is prepared according to the following method: subjecting an anti-aflatoxin monoclonal antibody and an activated europium-labeling reagent to an oscillatory reaction in a boric acid buffer solution for 2 hours or more, performing centrifuging to remove supernatant, and performing sealing to obtain a target product.

According to the above-described technical scheme, an activation method of the europium-labeling reagent comprises the steps: taking the europium labeling reagent, subjecting the europium labeling reagent to ultrasonic dispersion in a boric acid buffer solution, then slowly adding a carbodiimide solution, performing oscillating activation, performing centrifuging to remove supernatant, and performing redissolving by using a boric acid buffer solution for later use, wherein the activation time is 15-30 min.

According to the above-described technical scheme, a sealing fluid used in the sealing is a boric acid buffer solution containing 0.5-1% BSA.

According to the above-described technical scheme, the mass ratio of the europium-labeling reagent (on the basis of effective amount) to the aflatoxin monoclonal antibody is 1:(0.001-0.1), the mass ratio of the europium-labeling reagent (on the basis of effective amount) to the anti-carbaryl monoclonal antibody is 1:(0.001-0.1).

According to above-described technical scheme, a freeze-dried product of the europium-labeled anti-aflatoxin monoclonal antibody is prepared by adding the europium-labeled monoclonal antibody into an antibody protective liquid and then performing freeze-drying;

a freeze-dried product of the europium-labeled anti-carbaryl monoclonal antibody is prepared by adding the europium-labeled anti-carbaryl monoclonal antibody into an antibody protective liquid and then performing freeze-drying; and the antibody protective liquid is a water solution containing 0.01%-0.30 vt % (volume fraction) TWEEN® 20, 0.5-1.5 wt % sucrose and 0.1-1 wt % bovine serum albumin (BSA). It should be noted that TWEEN® 20 is generically referred to as polyoxyethylenesorbitan monolaurate.

According to the above-described technical scheme, the absorbent pad in the immunochromatographic time-resolved fluorescent test strip has a length of 15-35 mm and a width of 3-5 mm; the sample pad has a length of 12-18 mm and a width of 2-5 mm, and the overlapping length of each adjacent pads is 1-3 mm; in the immunochromatographic time-resolved fluorescent test strip, the spacing between the test line near the quality control line on the test pad and a top edge of the nitrocellulose membrane is 6-15 mm, the spacing between every two adjacent test lines is 1.5-4.5 mm, and the spacing between the test line near the quality control line and the quality control line is 4-10 mm; and the sample reaction vial is a 1-5 mL bayonet bottle.

According to the above-described technical scheme, in the immunochromatographic time-resolved fluorescent test strip and, the coating amount of the aflatoxin-bovine serum albumin conjugate for every centimeter of the test lines on the test pad is 0.4-0.8 μg, and the coating amount of the carbaryl-ovalbumin conjugate for every centimeter of the test lines is 0.8-1.0 μg; and the content of the europium-labeled anti-aflatoxin monoclonal antibody freeze-dried product in the sample reaction vial is 0.1-0.3 μg, and the content of the europium-labeled anti-carbaryl monoclonal antibody freeze-dried product in the sample reaction vial is 0.2-0.4 μg.

According to the above-described technical scheme, a preparation method for the time-resolved fluorescent test strip is as follows:

(1) cutting absorbent paper to obtain an absorbent pad;
(2) preparing a sample pad:
preparing the aflatoxin-bovine serum albumin conjugate and the carbaryl-ovalbumin conjugate into coating liquids with a concentration of 0.25-2 mg/mL, respectively coating the nitrocellulose membrane with the coating liquids in a membrane scratching manner at intervals to obtain two test lines, and then performing drying at 37-40° C. for 30-60 minutes; and
preparing the rabbit anti-mouse polyclonal antibody into a coating liquid with a concentration of 0.1-0.45 mg/mL, transversely coating the nitrocellulose membrane in a membrane scratching manner with the coating liquid to obtain a quality control line, wherein coating amount of the rabbit anti-mouse polyclonal antibody for every centimeter of the quality control line is 0.4-0.8 μg, and then performing drying at 37-40° C. for 30-60 minutes;
(3) preparing a sample pad:
soaking a fiberglass membrane in the sealing fluid, then taking out the soaked fiberglass membrane, drying the soaked fiberglass membrane at 37-40° C. for 4-10 hours to obtain the sample pad, and then placing the sample pad in a desiccator and storing the sample pad at room temperature; and
(4) assembling an immunochromatographic time-resolved fluorescent test strip:
successively stucking the absorbent pad, the test pad, and the sample pad onto one side of a paperboard from top to bottom in a manner that adjacent pads are overlapped and connected at junctions to obtain the immunochromatographic time-resolved fluorescent test strip.

According to the above-described technical scheme, every 10 mL of a coating buffer solution used in the preparation of an aflatoxin-bovine serum albumin conjugate coating liquid and a carbaryl-ovalbumin conjugate coating liquid in the preparation of the immunochromatographic time-resolved fluorescent test strip contains bovine serum albumin 0.1 g, sodium azide 0.002 g, sodium chloride 0.08 g, disodium hydrogen phosphate dodecahydrate 0.029 g, potassium chloride 0.002 g, and potassium dihydrogen phosphate 0.002 g;

every 10 mL of a coating buffer solution used in preparation of a rabbit anti-mouse polyclonal antibody coating liquid contains sodium azide 0.002 g, sodium chloride 0.08 g, disodium hydrogen phosphate dodecahydrate 0.029 g, potassium chloride 0.002 g, and potassium dihydrogen phosphate 0.002 g; and every 100 mL of the sealing fluid used in preparation of the immunochromatographic time-resolved fluorescent test strip contains ovalbumin 0.5-2 g, sucrose 2 g, sodium azide 0.02 g, sodium chloride 0.8 g, disodium hydrogen phosphate dodecahydrate 0.29 g, potassium chloride 0.02 g, and potassium dihydrogen phosphate 0.02 g.

Application of above-described immunochromatographic time-resolved fluorescence immunochromatography kit in content test of aflatoxin and carbaryl comprises the steps of: pretreating a sample to be detected to obtain a solution of the sample to be detected, adding the solution of the sample to be detected into a sample reaction vial, performing uniform mixing, inserting the time-resolved fluorescence test strip, performing a reaction for 6 min at a temperature of 37° C., and then performing testing by a time-resolved fluorescence tester to obtain a ratio of fluorescence intensity of test lines (T) to fluorescence intensity of the quality control line (C) on the immunochromatographic time-resolved fluorescence test strip; and acquiring contents of aflatoxin and carbaryl in the solution of the sample to be tested base on the respective relationship curves of the ratio (T/C) of the fluorescence intensity of the test lines to the fluorescence intensity of the quality control line on the immunochromatographic time-resolved fluorescent test strip with concentrations of aflatoxin and carbaryl, and finally performing conversion to obtain the contents of aflatoxin and carbaryl in the sample to be tested.

According to the above-described technical scheme, the respective relationship curves of the ratio (T/C) of the fluorescence intensity of the test lines to the fluorescence intensity of the quality control line of the immunochromatographic time-resolved fluorescent test strip with the concentrations of aflatoxin and carbaryl are obtained by using the following method:

(1) preparing aflatoxin standard substance solutions with a series of gradient concentrations, and carbaryl standard substance solutions with a series of concentrations;

(2) separately adding a moderate amount of each of the aflatoxin and carbaryl standard substance solutions with above-described gradient concentrations into sample reaction vials, performing uniform mixing, inserting immunochromatographic time-resolved fluorescence test strips, performing a reaction for 10 min at a temperature of 37° C., performing detecting with a time-resolved fluoroimmunoassay analyzer to obtain fluorescence intensities of the test lines (T) and the quality control line (C) on each immunochromatographic time-resolved fluorescence test strip, thereby obtaining a ratio (T/C) of the fluorescence intensity of the test lines to the fluorescence intensity of the quality control line of each immunochromatographic time-resolved fluorescence test strip; and (3) performing fitting to obtain the relationship curve of the ratio (T/C) of the fluorescence intensity of test lines to the fluorescence intensity of the quality control line of the immunochromatographic time-resolved fluorescence test strip with the concentrations of aflatoxin; and performing fitting to obtain the relationship curve of the ratio (T/C) of the fluorescence intensity of test lines to the fluorescence intensity of the quality control line of the immunochromatographic time-resolved fluorescence test strip with the concentrations of carbaryl.

Beneficial effects of the present application are as below:

(1) Aflatoxin and carbaryl are fast and simultaneously detected. The immunochromatographic time-resolved fluorescence immunochromatography kit provided by the present application may realize a synchronous and fast detection of two mycotoxins, aflatoxin and carbaryl, on one test paper strip, the antibodies used are both monoclonal antibodies, having a good specificity and high sensitivity, and no interference exists between the two antibodies; and the detection is simple and fast.

(2) Sensitivity is high. For the immunochromatographic time-resolved fluorescence immunochromatography kit provided by the present application, the lowest test limit for aflatoxin in a test solution is 0.02 ng/mL, the lowest test limit for carbaryl is 0.01 ng/mL, and the test limits may meet limit requirement on food in European Union.

(3) The sample pretreatment method is simple. The sample pretreatment only needs the steps of: adding a methanol-water extracting solution into the sample, conducting ultrasonic extraction for 5-10 minutes, then permitting standing for 5-10 minutes, taking and diluting supernatant, and performing test. The whole sample pretreatment progress is simple and fast.

BRIEF DESCRIPTION OF DRAWINGS

FIG. 1 is a structural schematic diagram of the immunochromatographic time-resolved fluorescent test strip for aflatoxin and carbaryl provided by the present application, wherein 1 represents the absorbent pad, 2 represents the test pad, 3 represents the sample pad, 4 represents the quality control line, 5 represents the carbaryl test line, and 6 represents the aflatoxin test line.

DETAILED DESCRIPTION OF EMBODIMENTS

Example 1. Acquisition of Anti-Carbaryl Monoclonal Antibody

Screening of Hybridoma Cell Strain Jnw1D2
1. Animal Immunization

Six 6 week-old BALB/c mice are purchased, bovine serum albumin (BSA) is coupled with 6-(1-naphthoxyformamide)-hexanoic acid (CNH) to obtain carbaryl complete antigen CNH-BSA, and the mice are immunized. During the first time of immunization, the carbaryl complete antigen and an equal volume of Freund's complete adjuvant are emulsified and then injected subcutaneously into multiple points of the nape of the mice. The second time of immunization is carried out three weeks later. A Freund's incomplete adjuvant and an equal volume of fumonisin complete antigen are emulsified and then injected subcutaneously into multiple points of the nape of the mice. The third time of immunization and the fourth time of immunization are conducted two weeks after the last time of immunization separately, in the same immunization manner as the second time of immunization. The same dose is adopted for four times of immunization, 100 µg per mouse only. On the 7th day after the third time of immunization, blood is collected from the caudal vein of the mice and serum is separated. The serum titer of the mice is monitored through indirect ELISA, the sensitivity of the serum of the mice is measured through indirect competitive ELISA, a mouse corresponding to the serum with higher titer and sensitivity is selected for the final booster immunization, and the immune dose is 2 times the previous dose.

2. Cell Fusion

Three days after the booster immunization, cell fusion is carried out with a conventional method using 50% (by weight) polyethylene glycol, namely PEG (molecular weight being 1450) as a fusion agent. Specifically, under an aseptic condition, the mice to be fused are killed by breaking the neck, spleen cells are isolated and mixed with murine myeloma cells SP2/0 at a ratio of 5:1, and the mixed cells are washed with an RPMI-1640 basal medium and centrifuged at 1200 rpm for 5 min. A supernatant is discarded, draining is conducted, 1 mL of PEG is added for fusion of 1 min, the RPMI-1640 basal medium is slowly added, centrifugation is conducted, a supernatant is discarded, a precipitation is fusion cells, resuspension is conducted with 20 mL of complete medium, suspended cells are added to 80 mL of semi-solid medium, and the mixture is added to a 6-well cell culture plate after uniform mixing at 2 mL/well, and then placed in a 37° C. CO2 incubator for culture.

the cell complete medium containing 1% HAT contains 20% (volume percentage) fetal calf serum, 75% (volume percentage) RPMI-1640 basal medium, 1% (weight percentage) L-glutamine, 1% (volume percentage) HEPES, 1% (volume percentage) Penicillin-Streptomycin (10000 units per milliliter of penicillin and 10000 µg per milliliter of streptomycin), 2% (volume percentage) growth factor (HFCS) and 1% (weight percentage) hypoxanthine-aminopterin-thymidine (i.e., HAT) and methylcellulose (purchased from Sigma-Aldrich company).

3. Screening and Cloning of Cell Strain 2-3 weeks after the cell fusion, when cell colonies grow to megascopic, colonies are picked out from the culture medium by a micropipette, transferred to a 96-well cell culture plate and cultivated by using HAT liquid, and when the cells grow to ⅔ of bottom of the well, culture supernatant is sucked out to conduct a test. A two-step screening method is employed: a first step adopts an indirect ELISA method to screen out the positive wells resistant to carbaryl but not resistant to a carrier protein BSA; and a second step adopts an indirect competitive ELISA method to detect the positive wells screened out in the first step, carbaryl is used as a competition agent, the wells with high absorbance and sensitivity are chosen (high absorbance means a well in which the competition agent is 0 namely final determined value of the positive control well is high, the high sensitivity means that the concentration of the competition agent when inhibition rate being 50% (i.e., IC50 value) is small), a subcloning is conducted by using limited dilution method, after the subcloning a test is conducted by using the two-step method, as such the subcloning is repeated 4-5 times, and then a hybridoma cell strain Jnw1D2 is obtained, and was stored/deposited under the terms of the Budapest Treaty at China Center for Type Culture Collection (CCTCC) on Mar. 29, 2016, with an accession preservation number of CCTCC NO: C201654.

4. Sequence Determination of Antibody Variable Region of Anti-Carbaryl Monoclonal Antibody Hybridoma Cell Strain Jnw1D2.
  (1) Total RNA extraction: total RNA capable of producing the hybridoma cell strain Jnw1D2 is extracted by using a total RNA extraction kit from TIANGEN according to the instruction manual;
  (2) Synthesis of cDNA: a first strand of cDNA is synthesized by reverse transcription according to a SuperScript™-2II reverse transcriptase instruction manual with the total RNA obtained in the step 1 as a template and oligo (dT) 15 as a primer, and the primer oligo (dT) 15 is purchased from Invitrogen; and
  (3) Cloning of variable region genes by PCR: primers are designed according to the conserved sites of mouse antibody gene sequences in GENBANK, to amplify the antibody heavy chain and light chain variable region genes with CDNA as a template. PCR procedures: 94° C. 30 s, 58° C. 45 s, 72° C. 1 min, amplification of 30 cycles, final extension for 10 min at 72° C. After PCR products are subjected to electrophoretic separation by 1% (by weight) sepharose, DNA fragments are purified and recovered with a kit and ligated into a support pMD18-T to be transformed into *Escherichia coli* DH5a competent cells, and positive clones are picked out and sent to Shanghai Sunny Biotechnology Co., Ltd. for sequencing. The sequences of the primers are as follows: the sequence of the primer of the heavy chain variable region is 5'-ACGACGTTGTAAAACGACGGC-3' (21 mer), as shown in SEQ ID. NO. 5, the sequences of the primers of the light chain variable region are 5'-ACGACGTTGTAAAACGACGGC-3' (21 mer), as shown in SEQ ID. NO. 6, and 5'-CAG GGG CCA GTG GAT AGA CAG ATG G-3' (21 mer), as shown in SEQ ID. NO. 7.

The obtained gene sequence results: the length of the coding gene sequence of the heavy chain variable region is 339 bp, the sequence is shown in SEQ ID NO: 1, it is deduced from the obtained gene sequence that the heavy chain variable region coded by the gene sequence is composed of 113 amino acids, and the sequence is shown in SEQ ID NO: 3; and the length of the coding gene sequence of the light chain variable region is 315 bp, the sequence is shown in SEQ ID NO: 2, it is deduced from the obtained gene sequence that the light chain variable region coded by the gene sequence is composed of 105 amino acids, and the sequence is shown in SEQ ID NO: 4.

5. Preparation, Purification, Subtypes and Characterization of Anti-Carbaryl Monoclonal Antibody The obtained anti-carbaryl monoclonal antibody hybridoma cell strain Jnw1D2 is injected into a BALB/c mouse previously treated with a Freund's incomplete adjuvant, the ascites of the mouse is collected, and the antibody is purified with an octanoic acid-ammonium sulfate method. Specifically, the ascites of the mouse is filtered through double-layer filter paper, the filtered ascites is centrifuged at 4° C. and 12000 r/min for more than 15 min, a supernatant is drawn, the supernatant is mixed with an acetate buffer with 4 times volume, n-octanoic acid is slowly added while stirring, the volume of n-octanoic acid required by per ml of ascites is 30-35 μL, and the mixture is mixed at room temperature for 30-60 min and stands at 4° C. for 2 h or more. Then centrifugation is conducted at 4° C. and 12000 r/min for 30 min or more, a precipitate is discarded, a resulting supernatant is filtered through double-layer filter paper, a phosphate buffer with 1/10 filtrate volume and with a molar concentration of 0.1 mol/L and a pH of 7.4 is added, the pH of the mixed liquid is adjusted with 2 mol/L sodium hydroxide solution to 7.4, ammonium sulfate is slowly added in an ice bath till the final concentration of ammonium sulfate reaches 0.277 g/mL, the mixture stands at 4° C. for 2 h or more, then centrifugation is conducted at 4° C. and 12000 r/min for 30 min or more, a supernatant is discarded, a resulting precipitate is resuspended with 0.01 mol/L phosphate buffer of 1/10 original volume of ascites with a pH of 7.4, placed in a dialysis bag and dialyzed with 0.01 mol/L PBS for two days, then dialysis is conducted with PB for two days, a protein solution in the dialysis bag is taken out and centrifuged, a supernatant is collected, a precipitate is discarded, and then the product is pre-frozen at −70° C. and then lyophilized in a lyophilizer. Lyophilized powder is collected, thus obtaining the purified anti-carbaryl monoclonal antibody;

the acetate buffer is obtained by adding water to 0.29 g of sodium acetate and 0.141 mL of acetic acid to 100 mL; the 0.01 mol/L phosphate buffer is obtained by adding water to 0.8 g of sodium chloride, 0.29 g of disodium hydrogen phosphate dodecahydrate, 0.02 g of potassium chloride and 0.02 g of potassium dihydrogen phosphate to 100 mL; and the 0.1 mol/L phosphate buffer is obtained by adding water to 8 g of sodium chloride, 2.9 g of disodium hydrogen phosphate dodecahydrate, 0.2 g of potassium chloride and 0.2 g of potassium dihydrogen phosphate to 100 mL.

Subtype of the anti-carbaryl monoclonal antibody secreted by the hybridoma cell strain Jnw1D2 identified by a commercially available subtype identification kit is IgG2b. The titer of the antibody determined by Enzyme Linked Immunosorbent Assay (ELISA) can reach $1.6 \times 10^4$. 50% inhibition concentration IC50 against carbaryl is 0.668 ng/kg, and no cross reaction with Carbofuran, Aldicarb, Methomyl, Metolcarb, Propoxur, Pirimicarb, Dimethacarb, Methiocarb, etc. presents (cross reaction rate <0.001). Through literature retrieval and comparison, the specificity exceeds the reported antibody.

Example 2 Acquisition of Anti-Aflatoxin Monoclonal Antibody

An anti-aflatoxin monoclonal antibody is secreted by a hybridoma cell strain 1C11 with an accession number of CCTCC NO. C201013. The hybridoma cell strain 1C11 was stored/deposited under the terms of the Budapest Treaty in CCTCC in Wuhan University, Wuhan, China, on Jul. 13, 2010 and has an accession number of CCTCC NO: C201013. The hybridoma cell strain 1C11 will be irrevocably and without restriction or condition released to the public upon the issuance of a patent would satisfy the deposit requirement made herein. The anti-aflatoxin monoclonal antibody is prepared in advance specifically according to the method reported in the patent with an authorization number of CN201010245095.5. The preparation method comprises the steps of: injecting a BALB/c mouse treated in advance by Freund's incomplete adjuvant with the obtained hybridoma cell strain 1C11, collecting ascites of the mouse, and performing purifying treatment to obtain the anti-aflatoxin monoclonal antibody. The purifying method is an octanoic acid-ammonium sulfate method, which comprises the specific operations of: filtering the mouse ascites with a double layer filter paper, centrifuging the filtered ascites at 4° C. and 12000 r/min for 15 minutes or more, sucking supernatant, mixing the supernatant with 4-fold volumes of acetate buffer, slowly adding n-octanoic acid under stirring, wherein the volume of n-octanoic acid for every milliliter ascites is 30-35 µL, conducting mixing at room temperature for 30-60 minutes, permitting standing at 4° C. for 2 hours or more, then conducting centrifuging at 4° C. and 12000 r/min for 30 minutes or more, discarding precipitates, filtering the obtained supernatant with double-layer filter paper, then adding phosphate buffer in a volume ⅒ of the volume of filtrate, and with a molar concentration of 0.1 mol/L and pH value 7.4, adjusting the pH value of the mixed liquid to 7 with 2 mol/L sodium hydroxide solution, pre-cooling the mixed liquid at 4.4° C., slowly adding ammonium sulfate until the final concentration of ammonium sulfate is 0.277 g/mL, permitting standing at 4° C. for 2 hours or more, then performing centrifuging at 4° C. and 12000 r/min for 30 minutes or more, discarding supernatant, re-suspending the obtained precipitate with 0.01 mol/L phosphate buffer with a volume ⅒ of the volume of original ascites, placing the re-suspended solution in a dialysis bag, performing dialysis with pure water, placing the fully dialyzed protein solution in a −70° C. refrigerator for refrigeration, then performing freeze-drying by a vacuum freeze drier, collecting the freeze-dried powder to obtain a purified anti-aflatoxin monoclonal antibody, and placing the antibody in a −20° C. refrigerator for later use; and the acetate buffer is obtained by adding water to 0.29 g of sodium acetate and 0.141 mL of acetic acid to 100 mL; the 0.01 mol/L phosphate buffer is obtained by adding water to 0.8 g of sodium chloride, 0.29 g of disodium hydrogen phosphate dodecahydrate, 0.02 g of potassium chloride and 0.02 g of potassium dihydrogen phosphate to 100 mL; and the 0.1 mol/L phosphate buffer is obtained by adding water to 8 g of sodium chloride, 2.9 g of disodium hydrogen phosphate dodecahydrate, 0.2 g of potassium chloride and 0.2 g of potassium dihydrogen phosphate to 100 mL.

Example 3: Time-Resolved Fluorescence Immunochromatography Kit for Simultaneously Detecting Aflatoxin and Carbaryl, and its Application A time-resolved fluorescence fluorescence immunochromatography kit for quantitatively detecting aflatoxin and carbaryl, comprising a fluorescent test strip, a europium-labeled anti-aflatoxin monoclonal antibody, a europium-labeled carbaryl monoclonal antibody, and a sample reaction vial; the fluorescent test strip is as shown in FIG. 1, comprising a paperboard, and an absorbent pad, a test pad and a sample pad are successively stuck onto one side of the paperboard from top to bottom, adjacent pads are overlapped and connected at the junctions, and the overlapping length is 1 mm; the absorbent pad in the immunochromatographic time-resolved fluorescent test strip has a length of 18 mm and a width of 4 mm; the test pad has a length of 25 mm and a width of 4 mm; the sample pad has a length of 15 mm and a width of 4 mm, and the overlapping length of adjacent pads is 1 mm; the test pad uses nitrocellulose membrane as a base pad, a quality control line and two test lines are arranged transversely on the nitrocellulose membrane from top to bottom, the quality control line is coated with a rabbit anti-mouse polyclone antibody with the coating amount of 0.4 µg/cm, the test lines are located below the quality control line, the number of the lines is 2, the test lines are respectively coated with an aflatoxin-bovine serum albumin conjugate and a carbaryl-ovalbumin conjugate with respective coating amounts of 0.4 µg/cm and 1 µg/cm, the spacing between the test line coated with the aflatoxin-bovine serum albumin conjugate and a top edge of the nitrocellulose membrane is 8 mm, the spacing between the quality control line and the test line coated with the aflatoxin-bovine serum albumin conjugate is 4 mm, and the spacing between the two test lines is 4 mm.

Acquisition of the Fluorescent Test Strip:
(1) Preparation of absorbent pad
absorbent paper is cut into a size specification of length 18 mm and width 4 mm to obtain an absorbent pad;
(2) Preparation of the test line
coating of the test pad:
by using a coating buffer solution, a carbaryl coated antigen (carbaryl-ovalbumin conjugate obtained by coupling 6-(1-naphthoxyformamide) hexanoic acid (CNH) with ovalbumin) is prepared into a coating liquid with a concentration of 1 mg/mL; at a position 12 mm from the top edge of the nitrocellulose membrane, the nitrocellulose membrane is coated with the coating liquid transversely in a membrane scratching manner to obtain a test line, wherein the coating amount of the coated antigen for every centimeter test line is 1.0 µg; and then drying is carried out at 37° C. for 60 minutes;
by using a coating buffer solution, an aflatoxin coated antigen (aflatoxin-bovine serum albumin) is prepared into a coating liquid with a concentration of 0.25 mg/mL; at a location 8 mm from the top edge of the nitrocellulose membrane, the nitrocellulose membrane is transversely coated with the coating liquid in a membrane scratching manner to obtain a test line, wherein the coating amount of the coated antigen for every centimeter test line is 0.4 µg; and then drying is carried out at 37° C. for 60 minutes;
every 10 mL of the coating buffer solution contains bovine serum albumin SA 0.1 g, sodium azide 0.002 g, sodium chloride 0.08 g, disodium hydrogen phosphate dodecahydrate 0.029 g, potassium chloride 0.002 g, and potassium dihydrogen phosphate 0.002 g;
coating of the quality control line:
the rabbit anti-mouse polyclonal antibody is prepared into a coating liquid with a concentration of 0.25 mg/mL by using a coating buffer solution; at a location 4 mm from the test line near the aflatoxin coated antigen, the nitrocellulose membrane transversely coated with the coating liquid in a membrane scratching manner to obtain a quality control line, wherein the coating amount of the rabbit anti-mouse polyclonal antibody for every centimeter of the quality control line is 0.4 µg; then and then drying is carried out at 37° C. for 2 hours;

the coating buffer solution is as below:
every 10 mL of the coating buffer solution contains albumin 0.1 g, sodium azide 0.002 g, sodium chloride 0.08 g, disodium hydrogen phosphate dodecahydrate 0.029 g, potassium chloride 0.002 g, and potassium dihydrogen phosphate 0.002 g;

the nitrocellulose membrane has a length of 25 mm and a width of 4 mm;

(3) Preparation of the sample pad:
a fiberglass membrane is cut into a size specification of length 15 mm and width 4 mm, soaked in a sealing fluid, taken out, and dried at 37° C. for 6 hours to obtain the sample pad, and then the sample pad is placed in a desiccator and stored at room temperature;

the sealing fluid is prepared by adding water to 2.9 g of disodium hydrogen phosphate dodecahydrate, 0.3 g of sodium dihydrogenphosphate dihydrate, 1.0 g of TWEEN® 20, 1.0 g of polyvinylpyrrolidone (PVPK-30), 0.25 g of EDTA, 0.5 g of bovine serum albumin (BSA) and 0.02 g of sodium azide to 100 mL; and (4) Assembly of the fluorescent test strip:
the absorbent pad, the test pad and the sample pad are successively stuck onto one side of the paperboard from top to bottom to obtain the fluorescent test strip, wherein adjacent pads are overlapped and connected at junctions, and the overlapping length is 1 mm.

Acquisition of the Europium-Labeled Anti-Aflatoxin Monoclonal Antibody:

800 µL of 0.2 mol/L boric acid buffer solution (pH 8.18) is taken, 200 µL of a europium-labeling reagent (particle size 100 nm, solid content 1%) is added, and shaking for uniform mixing is carried out. Ultrasound treatment is carried out for 3 seconds. 40 µL of 15 mg/mL EDC solution is added, and shaking for uniform mixing is carried out for 15 minutes. Centrifuging at 13000 r/min and 10° C. is carried out for 10 minutes, the supernatant is removed, 1 mL of the boric acid buffer solution is added for re-dissolving, shaking for uniform mixing is carried out, and ultrasound treatment is carried out for 3 seconds. 20 µg of the anti-aflatoxin monoclonal antibody is added, uniform mixing is carried out, and shaking table treatment at 250 r/min and 25° C. is carried out overnight. Centrifuging is carried out again, the supernatant is removed, 1 mL of the boric acid buffer solution containing 0.5% BSA is added for re-dissolving, shaking for uniform mixing is carried out, ultrasound treatment is carried out for 10 minutes, and shaking table treatment at 25° C. is carried out for 2 hours to obtain a target product namely the europium-labeled anti-aflatoxin monoclonal antibody. The above-described europium-labeling reagent can be purchased from but not limited to Shanghai Youni Biotechnology Co., Ltd.

Acquisition of the Europium-Labeled Anti-Carbaryl Monoclonal Antibody:

800 µL of 0.2 mol/L boric acid buffer solution (pH 8.18) is taken, 200 µL of a europium-labeling reagent (particle size 100 nm, solid content 1%) is added, and shaking for uniform mixing is carried out. Ultrasound treatment is carried out for 3 seconds. 40 µL of 15 mg/mL EDC solution is added, and shaking for uniform mixing is carried out for 15 minutes. Centrifuging at 13000 r/min and 10° C. is carried out for 10 minutes, the supernatant is removed, 1 mL of the boric acid buffer solution is added for re-dissolving, shaking for uniform mixing is carried out, and ultrasound treatment is carried out for 3 seconds. 20 µg of the anti-carbaryl monoclonal antibody is added, uniform mixing is carried out, and shaking table treatment at 250 r/min and 25° C. is carried out overnight. Centrifuging is carried out again, the supernatant is removed, 1 mL of the boric acid buffer solution containing 0.5% BSA is added for re-dissolving, shaking for uniform mixing is carried out, ultrasound treatment is carried out for 10 minutes, and shaking table treatment at 25° C. is carried out for 2 hours to obtain a target product namely the europium-labeled anti-aflatoxin monoclonal antibody. The above-described europium-labeling reagent can be purchased from but not limited to Shanghai Youni Biotechnology Co., Ltd.

Acquisition of the sample reaction vial: the above-described europium-labeled anti-aflatoxin monoclonal antibody at a ratio of 1:300 (V:V), and the above-described europium-labeled anti-carbaryl monoclonal antibody at a ratio of 1:250 (V:V) are added to a certain volume of antibody protective liquid, freeze-drying in a freeze-drier is performed, 0.1 µg of the europium-labeled anti-aflatoxin monoclonal antibody freeze-dried product and 0.3 µg of the europium-labeled anti-carbaryl monoclonal antibody freeze-dried product are taken, and added in a sample reaction vial. The antibody protective liquid contains 0.01 vt % TWEEN® 20, 0.5 wt % sucrose and 1 wt % bovine serum albumin (BSA).

Application of the Above-Described Immunochromatographic Time-Resolved Fluorescent Test Strip in Quantitative Test of Aflatoxin and Carbaryl:

1. Establishment of relationship curves of ratio (T/C) of the fluorescence intensity of the test lines to the fluorescence intensity of the quality control line on the immunochromatographic time-resolved fluorescent test strip with the concentrations of aflatoxin and carbaryl:

(1) a pretreatment is conducted to the cereal being negative for aflatoxin and carbaryl by high performance liquid chromatography (HPLC) test. 25 g of a cereal sample is taken, 100 mL of 80% methanol water solution is added, a homogenization extraction is conducted for 5 minutes, standing is conducted, filtering with double-layer filter paper is conducted, and the filtrate is collected, and diluted at a ratio of 1:4;

(2) the above-described cereal sample diluted solution is labeled with a standard substance, and a mixed standard substance solution is prepared. Aflatoxin/carbaryl is added at a ratio of 1:10 to prepare aflatoxin and carbaryl mixed standard substance solutions for each gradient concentration. The aflatoxin concentrations are 1.5 ng/ml, 0.5 ng/ml, 0.15 ng/ml, 0.05 ng/ml, 0.015 ng/mL, 0.005 ng/mL, and the carbaryl concentrations are 15 ng/ml, 5 ng/ml, 1.5 ng/ml, 0.5 ng/mL, 0.15 ng/ml, 0.05 ng/ml;

(3) 300 µL of the atoxin and carbaryl mixed standard substance solution is taken and added in a sample vial, then added to a sample reaction vial containing the europium-labeled monoclonal antibodies, uniform mixing is conducted, one end of each fluorescent test strip sample pad is inserted into the reaction vial, a reaction at 37° C. is performed for 10 minutes, and test by a test instrument of time-resolved fluoroimmunoassay analyzer with an excitation wavelength of 365 nm and an emission wavelength of 615 nm is carried out. A ratio (T/C) of the fluorescence intensity of the test lines to the fluorescence intensity of the quality control line on each fluorescent test strip is obtained; and (4) aflatoxin and carbaryl standard substance concentration is used as a horizontal ordinate, and the ratio of the fluorescence intensity of the test lines and the fluorescence intensity of the quality control line of each concentration standard substance solution (i.e., T/C) is used as a vertical ordinate to obtain a relationship curve by fitting. Effective test range of the method is 0.1-1 ng/mL for carbaryl and 0.02-0.85 ng/ml for aflatoxin.

2. Labeled recovery experiment of aflatoxin and carbaryl contents in cereal sample:

25 g of a cereal sample is taken, and 20 mL of 80% methanol water solution is added, a homogenization extraction is conducted for 5 minutes, standing and filtering with double-layer filter paper are carried out, and the filtrate is collected, and diluted at a ratio of 1:1. Aflatoxin (carbaryl) standard substance is respectively and accurately added at 0.005 ng/ml, 0.01 ng/ml and 0.1 ng/ml (0.05 ng/ml, 0.1 ng/ml and 1 ng/ml), 300 μL of the above-described test liquid sample to be tested is taken and added into a sample reaction vial containing the europium-labeled monoclonal antibody, uniform mixing is carried out, one end of the fluorescent test strip sample pad is inserted into the reaction vial, a reaction is carried out at 37° C. for 10 minutes, and the fluorescent test strip is detected by a test instrument. The test instrument is time-resolved fluoroimmunoassay analyzer with an excitation wavelength of 365 nm and an emission wavelength of 615 nm. A ratio (T/C) of time-resolved fluorescence intensity of test lines (T) to time-resolved fluorescence intensity of the quality control line (C) on each fluorescence test strip is obtained; and then by substituting the ratio (T/C) into the above-described relationship curves of ratio (T/C) of the time-resolved fluorescence intensity of the test lines to the time-resolved fluorescence intensity of the quality control line on the fluorescent test strip with the standard substance concentrations, the concentrations of aflatoxin and carbaryl in the sample solution are obtained, and then the contents of aflatoxin and carbaryl in the sample can be calculated on the basis of dilution ratio. The labeled recovery rates of aflatoxin in cereal sample are successively: 106.5%, 90.2%, and 86.1%; and the labeled recovery rates of carbaryl are successively: 104.1%, 89.5%, and 83.7%.

Example 4

A time-resolved fluorescence immunochromatography kit for quantitatively detecting aflatoxin and carbaryl, comprising a fluorescent test strip, a europium-labeled anti-aflatoxin monoclonal antibody, a europium-labeled carbaryl monoclonal antibody, and a sample reaction vial; the fluorescent test strip comprises a paperboard, an absorbent pad, a test pad and a sample pad are successively stuck onto one side of the paperboard from top to bottom, adjacent pads are overlapped and connected at the junctions, and the overlapping length is 2 mm; the absorbent pad in the immunochromatographic time-resolved fluorescent test strip has a length of 18 mm and a width of 3 mm; the test pad has a length of 25 mm and a width of 3 mm; the sample pad has a length of 15 mm and a width of 3 mm, and the overlapping length of each adjacent pads is 2 mm; and the test pad uses the nitrocellulose membrane as a base pad, a quality control line and two test lines are arranged transversely on the nitrocellulose membrane from top to bottom, the quality control line is coated with a rabbit anti-mouse polyclonal antibody, the coating amount is 0.6 μg/cm, the test lines are located below the quality control line, the number of the test lines is 2, the test lines are respectively coated with an aflatoxin-bovine serum albumin conjugate and a carbaryl-ovalbumin conjugate, the coating amounts are respectively 0.6 μg/cm and 0.6 μg/cm, the spacing between the test line near the quality control line and a top edge of the nitrocellulose membrane is 12 mm, the spacing between the quality control line and the first test line is 3 mm, and the spacing between the two test lines is 3 mm.

0.2 μg of a europium-labeled anti-aflatoxin monoclonal antibody freeze-dried product and 0.2 μg of a europium-labeled anti-carbaryl monoclonal antibody freeze-dried product are put into the sample reaction vial. The antibody protective liquid is water solution of 0.1 vt % (volume fraction) TWEEN® 20, 1 wt % sucrose and 0.5 wt % bovine serum albumin (BSA); in the preparation of the anti-aflatoxin monoclonal antibody, the mass ratio of the europium-labeling reagent to the aflatoxin monoclonal antibody (on the basis of effective amount) is 1:0.1, and in preparation of the anti-carbaryl monoclonal antibody, the mass ratio of the europium-labeling reagent to the carbarylantibody (on the basis of effective amount) is 1:0.1.

Labeled recovery experiment of aflatoxin and carbaryl contents in nut sample: 5 g of a nut sample is taken, and 20 mL of 80% methanol water solution is added, a homogenization extraction is conducted for 5 minutes, standing and filtering with double-layer filter paper are carried out, and the filtrate is collected, and diluted at a ratio of 1:1. Aflatoxin (carbaryl) standard substance is respectively and accurately added at 0.005 ng/ml, 0.01 ng/ml and 0.1 ng/ml (0.05 ng/mL, 0.1 ng/mL and 1 ng/mL), 300 μL of the above-described test liquid sample to be tested is taken and added into a sample reaction vial containing the europium-labeled monoclonal antibody, uniform mixing is carried out, one end of the fluorescent test strip sample pad is inserted into the reaction vial, a reaction is carried out at 37° C. for 10 minutes, and the fluorescent test strip is detected by a test instrument. The test instrument is time-resolved fluoroimmunoassay analyzer with an excitation wavelength of 365 nm and an emission wavelength of 615 nm. A ratio (T/C) of time-resolved fluorescence intensity of test lines (T) to time-resolved fluorescence intensity of the quality control line (C) on each fluorescence test strip is obtained; and then by substituting the ratio (T/C) into the above-described relationship curves of ratio (T/C) of the time-resolved fluorescence intensity of the test lines to the time-resolved fluorescence intensity of the quality control line on the fluorescent test strip with the standard substance concentrations, the concentrations of aflatoxin and carbaryl in the sample solution are obtained, and then the contents of aflatoxin and carbaryl in the sample can be calculated on the basis of dilution ratio. The determined aflatoxin labeled recovery rates in the nut sample are successively: 103.0%, 92.0%, and 85.4%; and the carbaryl labeled recovery rates are successively: 108.5%, 91.5%, and 80.9%.

What is claimed is:

1. An immunochromatographic time-resolved fluorescence immunochromatography kit for simultaneously detecting mixed pollution of aflatoxin and carbaryl, comprising:

an immunochromatographic time-resolved fluorescent test strip, and a sample reaction vial containing a europium-labeled anti-aflatoxin monoclonal antibody freeze-dried product and a europium-labeled anti-carbaryl monoclonal antibody freeze-dried product, wherein the immunochromatographic time-resolved fluorescent test strip includes a paperboard, an absorbent pad (1), a test pad (2) and a sample pad (3) successively stacked onto one side of the paperboard from one edge to another edge of the paperboard, wherein adjacent pads are overlapped and connected at junctions, the test pad (2) uses a nitrocellulose membrane as a base pad, a quality control line (4) and test lines (5, 6) are transversely arranged on the nitrocellulose membrane from the one edge to the another edge of the paperboard, the quality control line (4) is coated with a rabbit anti-mouse polyclonal antibody, the test lines are located below the quality control line, the number of the test lines is 2, and the test lines (5, 6) are respectively coated with a carbaryl-ovalbumin conjugate and an aflatoxin-bovine serum albumin conjugate; and wherein the anti-carbaryl monoclonal antibody is secreted by a hybridoma cell strain Jnw1D2 that is deposited under the terms of the Budapest Treaty in CCTCC with an accession number of CCTCC NO.

C201654; and wherein the anti-aflatoxin monoclonal antibody is secreted from a hybridoma cell strain 1C11 that is deposited under the terms of the Budapest Treaty in CCTCC with an accession number of CCTCC NO. C201013.

2. The immunochromatographic time-resolved fluorescence immunochromatography kit according to claim 1, wherein the europium-labeled anti-carbaryl monoclonal antibody is prepared according to the following method: subjecting an anti-carbaryl monoclonal antibody and an activated europium-labeling reagent to an oscillatory reaction in a boric acid buffer solution for 2 hours or more, performing centrifuging to remove supernatant, and performing sealing to obtain the europium-labeled anti-carbaryl monoclonal antibody; and the europium-labeled anti-aflatoxin monoclonal antibody is prepared according to the following method: subjecting an anti-aflatoxin monoclonal antibody and an activated europium-labeling reagent to an oscillatory reaction in a boric acid buffer solution for 2 hours or more, performing centrifuging to remove supernatant, and performing sealing to obtain the europium-labeled anti-aflatoxin monoclonal antibody.

3. The immunochromatographic time-resolved fluorescence immunochromatography kit according to claim 2, wherein:
an activation method of the europium-labeling reagent comprises the steps: taking the europium labeling reagent, subjecting the europium labeling reagent to ultrasonic dispersion in a boric acid buffer solution, then slowly adding a carbodiimide solution, performing oscillating activation, performing centrifuging to remove supernatant, and performing redissolving by using a boric acid buffer solution for later use, wherein the activation time is 15-30 min; and performing sealing by using a sealing fluid of a boric acid buffer solution containing 0.5-1% BSA.

4. The immunochromatographic time-resolved fluorescence immunochromatography kit according to claim 2, wherein a mass ratio of the europium-labeling reagent to the anti-aflatoxin monoclonal antibody is 1:(0.001-0.1), and the mass ratio of the europium-labeling reagent to anti-carbaryl monoclonal antibody is 1:(0.001-0.1).

5. The immunochromatographic time-resolved fluorescence immunochromatography kit according to claim 1, wherein the europium-labeled anti-aflatoxin monoclonal antibody freeze-dried product is prepared by adding the europium-labeled anti-aflatoxin monoclonal antibody into an antibody protective liquid and performing freeze-drying;
wherein the europium-labeled anti-carbaryl monoclonal antibody freeze-dried product is prepared by adding the europium-labeled anti-carbaryl monoclonal antibody into an antibody protective liquid and performing freeze-drying; and
wherein the antibody protective liquid is a water solution of 0.01%-0.30 vt % (volume fraction) TWEEN® 20, 0.5-1.5 wt % sucrose and 0.1-1 wt % bovine serum albumin (BSA).

6. The immunochromatographic time-resolved fluorescence immunochromatography kit according to claim 1, wherein the absorbent pad (1) in the immunochromatographic time-resolved fluorescent test strip has a length of 15-35 mm and a width of 3-5 mm; the sample pad (3) has a length of 12-18 mm and a width of 2-5 mm, an overlapping length of adjacent pads is 1-3 mm; in the immunochromatographic time-resolved fluorescent test strip, a spacing between the test line (6) near the quality control line (4) and an edge of the nitrocellulose membrane is 6-15 mm, a spacing between every two adjacent test lines (5, 6) is 1.5-4.5 mm, and a spacing between the test line (6) near the quality control line (4) and the quality control line (4) is 4-10 mm; and the sample reaction vial is a 1-5 mL bayonet bottle.

7. The immunochromatographic time-resolved fluorescence immunochromatography kit according to claim 1, wherein in the immunochromatographic time-resolved fluorescent test strip, a coating amount of the aflatoxin-bovine serum albumin conjugate for every centimeter of the test lines (5, 6) on the test pad (2) is 0.4-0.8 μg, and a coating amount of the carbaryl-ovalbumin conjugate for every centimeter of the test lines (5, 6) is 0.8-1.0 μg; and a content of the europium-labeled anti-aflatoxin monoclonal antibody freeze-dried product in the sample reaction vial is 0.1-0.3 μg, and a content of the europium-labeled anti-carbaryl monoclonal antibody freeze-dried product in the sample reaction vial is 0.2-0.4 μg.

8. A preparation method of the immunochromatographic time-resolved fluorescence immunochromatographic kit according to claim 1, wherein the method comprises the steps of:
(a) cutting an absorbent paper to obtain the absorbent pad (1);
(b) preparing the test pad (2):
preparing the aflatoxin-bovine serum albumin conjugate and the carbaryl-ovalbumin conjugate into coating liquids with a concentration of 0.25-2 mg/mL, respectively coating the nitrocellulose membrane with the coating liquids in a membrane scratching manner at intervals to obtain the two test lines (5, 6), and then performing drying at 37-40° C. for 30-60 minutes; and
preparing the rabbit anti-mouse polyclonal antibody into a coating liquid with a concentration of 0.1-0.45 mg/mL, transversely coating the nitrocellulose membrane in a membrane scratching manner with the coating liquid to obtain the quality control line (4), wherein coating amount of the rabbit anti-mouse polyclonal antibody for every centimeter of the quality control line is 0.4-0.8 μg, and then performing drying at 37-40° C. for 30-60 minutes;
(c) preparing the sample pad (3):
soaking a fiberglass membrane in the sealing fluid, then taking out the soaked fiberglass membrane, drying the soaked fiberglass membrane at 37-40° C. for 4-10 hours to obtain the sample pad (3), and then placing the sample pad in a desiccator and storing the sample pad at room temperature; and
(d) assembling an immunochromatographic time-resolved fluorescent test strip:
successively stacking the absorbent pad (1), the test pad (2), and the sample pad (3) onto one side of a paperboard from the one edge to the another edge of the paperboard in a manner that adjacent pads are overlapped and connected at junctions to obtain the immunochromatographic time-resolved fluorescent test strip;
every 10 mL of a coating buffer solution used in the preparation of an aflatoxin-bovine serum albumin conjugate coating liquid and a carbaryl-ovalbumin conjugate coating liquid in the preparation of the immunochromatographic time-resolved fluorescent test strip contains bovine serum albumin 0.1 g, sodium azide 0.002 g, sodium chloride 0.08 g, disodium hydrogen phosphate dodecahydrate 0.029 g, potassium chloride 0.002 g, and potassium dihydrogen phosphate 0.002 g;
every 10 mL of a coating buffer solution used in the preparation of the rabbit anti-mouse polyclonal antibody contains sodium azide 0.002 g, sodium chloride 0.08 g, disodium hydrogen phosphate dodecahydrate 0.029 g, potassium chloride 0.002 g, and potassium dihydrogen phosphate 0.002 g; and every 100 mL of the sealing fluid used in the preparation of the immunochromatographic time-resolved fluorescent test strip contains ovalbumin 0.5-2 g, sucrose 2 g, sodium azide 0.02 g, sodium chloride 0.8 g, disodium hydrogen phosphate dodecahydrate 0.29 g, potassium chloride 0.02 g, and potassium dihydrogen phosphate 0.02 g.

9. A method of using the immunochromatographic time-resolved fluorescence immunochromatography kit according to claim 1 in content test of aflatoxin and carbaryl, wherein the method comprises the steps of: pretreating a sample to be detected to obtain a solution of the sample to be detected, adding the solution of the sample to be detected into the sample reaction vial, performing uniform mixing, inserting the time-resolved fluorescence test strip, performing a reaction for 6 min at a temperature of 37° C., and then performing testing by a time-resolved fluorescence tester to obtain a ratio of fluorescence intensity of test lines (T) to fluorescence intensity of the quality control line (C) on the immunochromatographic time-resolved fluorescence test strip; and acquiring contents of aflatoxin and carbaryl in the solution of the sample to be tested based on respective relationship curves of the ratio (T/C) of the fluorescence intensity of the test lines to the fluorescence intensity of the quality control line on the immunochromatographic time-resolved fluorescent test strip with concentrations of aflatoxin and carbaryl.

10. The method according to claim 9, wherein the respective relationship curves of the ratio (T/C) of the fluorescence intensity of the test lines to the fluorescence intensity of the quality control line of the immunochromatographic time-resolved fluorescent test strip with the concentrations of aflatoxin and carbaryl are obtained by using the following method:

(a) preparing aflatoxin standard substance solutions with a series of gradient concentrations, and carbaryl standard substance solutions with a series of concentrations;

(b) separately adding a moderate amount of each of the aflatoxin and carbaryl standard substance solutions with above-described gradient concentrations into the sample reaction vial, performing uniform mixing, inserting immunochromatographic time-resolved fluorescence test strips, performing a reaction for 10 min at a temperature of 37° C., and performing detecting with a time-resolved fluoroimmunoassay analyzer to obtain fluorescence intensities of the test lines (T) and the quality control line (C) on each immunochromatographic time-resolved fluorescence test strip, thereby obtaining a ratio (T/C) of the fluorescence intensity of the test lines to the fluorescence intensity of the quality control line of each immunochromatographic time-resolved fluorescence test strip; and (c) performing fitting to obtain the relationship curve of the ratio (T/C) of the fluorescence intensity of test lines to the fluorescence intensity of the quality control line of the immunochromatographic time-resolved fluorescence test strip with the concentrations of aflatoxin; and performing fitting to obtain the relationship curve of the ratio (T/C) of the fluorescence intensity of test lines to the fluorescence intensity of the quality control line of the immunochromatographic time-resolved fluorescence test strip with the concentrations of carbaryl.

* * * * *

SEQUENCE LISTING

<160> NUMBER OF SEQ ID NOS: 7

<210> SEQ ID NO 1
<211> LENGTH: 339
<212> TYPE: DNA

<213> ORGANISM: Mouse

<400> SEQUENCE: 1

```
caggtgcagc tgaaggagtc aggacctggc ctggtggcgc cctcacagag      50
cctgtccatc acttgcactg tctctgggct ttcattaacc agctatggtg     100
tacactgggt tcgtcaggcc ccaggaaagg gtctggagtg gctgggagta     150
atttggggtg gtggaaacac aaattataat tcggctctca tgtccagact     200
gagcatcagc aaagacaact ccaggagcca agttttctta agaatgaaca     250
gtctgcaaat tgatgacaca gccatgtact attgtgccag aggcaggatg     300
gactactggg gtcaaggaac ctcagtcacc gtctcgtca               339
```

<210> SEQ ID NO 2
<211> LENGTH: 315
<212> TYPE: DNA
<213> ORGANISM: Mouse

<400> SEQUENCE: 2

```
gacatcaaga tgacccagtc tccatcttcc atgtatgcat ctctaggaga      50
aagagtcact atcacttgca aggcgagtca ggacattagt agctatttag     100
gctggttaca gcagaaacca gggaaatctc ctaagaccct gatctatcgt     150
gcaaacacat tggtagaagg ggtcccatcc agattcagtg gcagtggatc     200
tgggaagat tattctctca ccatcagcag cctggagtat gaagatatgg     250
gaatttatta ttgtctacag tatgatgagt ttccgtacac gttcggaggg     300
gggaccaagc tggaa                                           315
```

<210> SEQ ID NO 3
<211> LENGTH: 113
<212> TYPE: PRT
<213> ORGANISM: Mouse

<400> SEQUENCE: 3

```
Gln Val Gln Leu Lys Glu Ser Gly Pro Gly Leu Val Ala Pro Ser
1               5                   10                  15

Gln Ser Leu Ser Ile Thr Cys Thr Val Ser Gly Leu Ser Leu Thr
                20                  25                  30

Ser Tyr Gly Val His Trp Val Arg Gln Ala Pro Gly Lys Glu Leu
                35                  40                  45

Glu Trp Leu Gly Val Ile Trp Gly Gly Gly Asn Thr Asn Tyr Asn
                50                  55                  60

Ser Ala Leu Met Ser Arg Leu Ser Ile Ser Lys Asp Asn Ser Arg
                65                  70                  75

Ser Gln Val Phe Leu Arg Met Asn Ser Leu Gln Ile Asp Asp Thr
                80                  85                  90

Ala Met Tyr Tyr Cys Ala Arg Gly Arg Met Asp Tyr Trp Gly Gln
                95                  100                 105

Gly Thr Ser Val Thr Val Ser Ser
                110
```

<210> SEQ ID NO 4
<211> LENGTH: 105
<212> TYPE: PRT
<213> ORGANISM: Mouse

```
<400> SEQUENCE: 4

Asp Ile Lys Met Thr Gln Ser Pro Ser Ser Met Tyr Ala Ser Leu
1               5                   10                  15

Gly Glu Arg Val Thr Ile Thr Cys Lys Ala Ser Gln Asp Ile Ser
                20                  25                  30

Ser Tyr Leu Gly Thr Leu Gln Gln Lys Pro Gly Lys Ser Pro Lys
                35                  40                  45

Thr Leu Ile Tyr Arg Ala Asn Thr Leu Val Glu Gly Val Pro Ser
                50                  55                  60

Arg Phe Ser Gly Ser Gly Ser Gly Glu Asp Tyr Ser Leu Thr Ile
                65                  70                  75

Ser Ser Leu Glu Thr Glu Asp Met Gly Ile Tyr Tyr Cys Leu Gln
                80                  85                  90

Tyr Asp Glu Phe Pro Tyr Thr Phe Gly Gly Gly Thr Lys Leu Glu
                95                  100                 105

<210> SEQ ID NO 5
<211> LENGTH: 21
<212> TYPE: DNA
<213> ORGANISM: Artificial
<220> FEATURE:
<223> OTHER INFORMATION: Synthesized

<400> SEQUENCE: 5
acgacgttgt aaaacgacgg c                                          21

<210> SEQ ID NO 6
<211> LENGTH: 21
<212> TYPE: DNA
<213> ORGANISM: Artificial
<220> FEATURE:
<223> OTHER INFORMATION: Synthesized

<400> SEQUENCE: 6
acgacgttgt aaaacgacgg c                                          21

<210> SEQ ID NO 7
<211> LENGTH: 25
<212> TYPE: DNA
<213> ORGANISM: Artificial
<220> FEATURE:
<223> OTHER INFORMATION: Synthesized

<400> SEQUENCE: 7
caggggccag tggatagaca gatgg                                      25
```